United States Patent
Bouchet-Marquis et al.

(10) Patent No.: US 9,627,176 B2
(45) Date of Patent: Apr. 18, 2017

(54) FIDUCIAL FORMATION FOR TEM/STEM TOMOGRAPHY TILT-SERIES ACQUISITION AND ALIGNMENT

(71) Applicant: FEI Company, Hillsboro, OR (US)

(72) Inventors: Cedric Bouchet-Marquis, Hillsboro, OR (US); Liang Zhang, Portland, OR (US); Lee Pullan, Portland, OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/989,419

(22) Filed: Jan. 6, 2016

(65) Prior Publication Data

US 2017/0025246 A1    Jan. 26, 2017

Related U.S. Application Data

(60) Provisional application No. 62/196,246, filed on Jul. 23, 2015.

(51) Int. Cl.
*H01J 37/22* (2006.01)
*H01J 37/28* (2006.01)

(52) U.S. Cl.
CPC ............ *H01J 37/222* (2013.01); *H01J 37/28* (2013.01)

(58) Field of Classification Search
USPC .................. 250/307, 306, 309, 310, 311
See application file for complete search history.

(56) References Cited

U.S. PATENT DOCUMENTS

| | | | |
|---|---|---|---|
| 7,442,924 B2 | 10/2008 | Giannuzzi et al. | |
| 7,884,326 B2 | 2/2011 | Van De Water et al. | |
| 2010/0084555 A1* | 4/2010 | Luo | G01N 1/28 250/311 |
| 2010/0288925 A1 | 11/2010 | Principe | |

(Continued)

FOREIGN PATENT DOCUMENTS

EP         2056332 A1      5/2009

OTHER PUBLICATIONS

Hayashida, M. et al., "High-precision alignment of electron tomography tilt series using markers formed in helium-ion microscope," Micron, Jul. 2013, pp. 29-34, vol. 50.

(Continued)

*Primary Examiner* — Kiet T Nguyen
(74) *Attorney, Agent, or Firm* — Scheinberg & Associates, P.C.; Michael O. Scheinberg

(57) ABSTRACT

Provided are methods to improve tomography by creating fiducial holes using charged particle beams, and using the fiducial holes to improve the sample positioning, acquisition, alignment, reconstruction, and visualization of tomography data sets. Some versions create fiducial holes with an ion beam during the process of milling the sample. Other versions create in situ fiducial holes within the TEM using the electron beam prior to acquiring a tomography data series. In some versions multiple sets of fiducial holes are made, positioned strategically around a region of interest. The fiducial holes may be employed to properly position the features of interest during the acquisition, and later to help better align the tilt-series, and improve the accuracy and resolution of the final reconstruction. The operator or software may identify the holes to be tracked with tomography feature tracking techniques.

26 Claims, 12 Drawing Sheets

(56) References Cited

U.S. PATENT DOCUMENTS

| | | |
|---|---|---|
| 2012/0001068 A1 | 1/2012 | He et al. |
| 2014/0070095 A1 | 3/2014 | Schoenmakers et al. |
| 2014/0145077 A1 | 5/2014 | Schoenmakers et al. |
| 2015/0069231 A1 | 3/2015 | Luecken et al. |
| 2015/0253353 A1 | 9/2015 | Alvis |

OTHER PUBLICATIONS

Miller, M.K. et al., "Strategies for fabricating atom probe specimens with a dual beam FIB," Ultramicroscopy, Mar. 2005, pp. 287-298, vol. 102, Issue 4.

\* cited by examiner

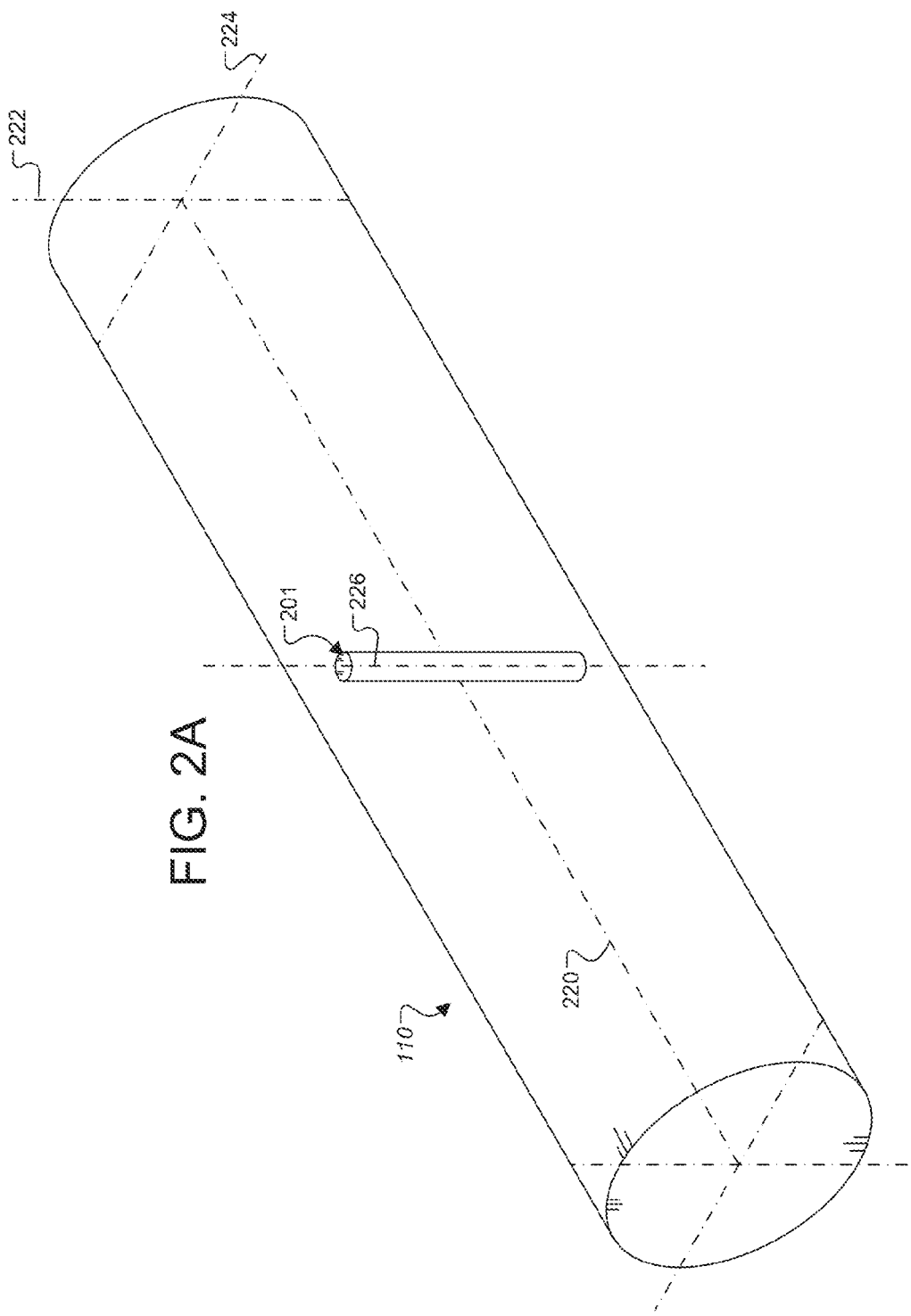

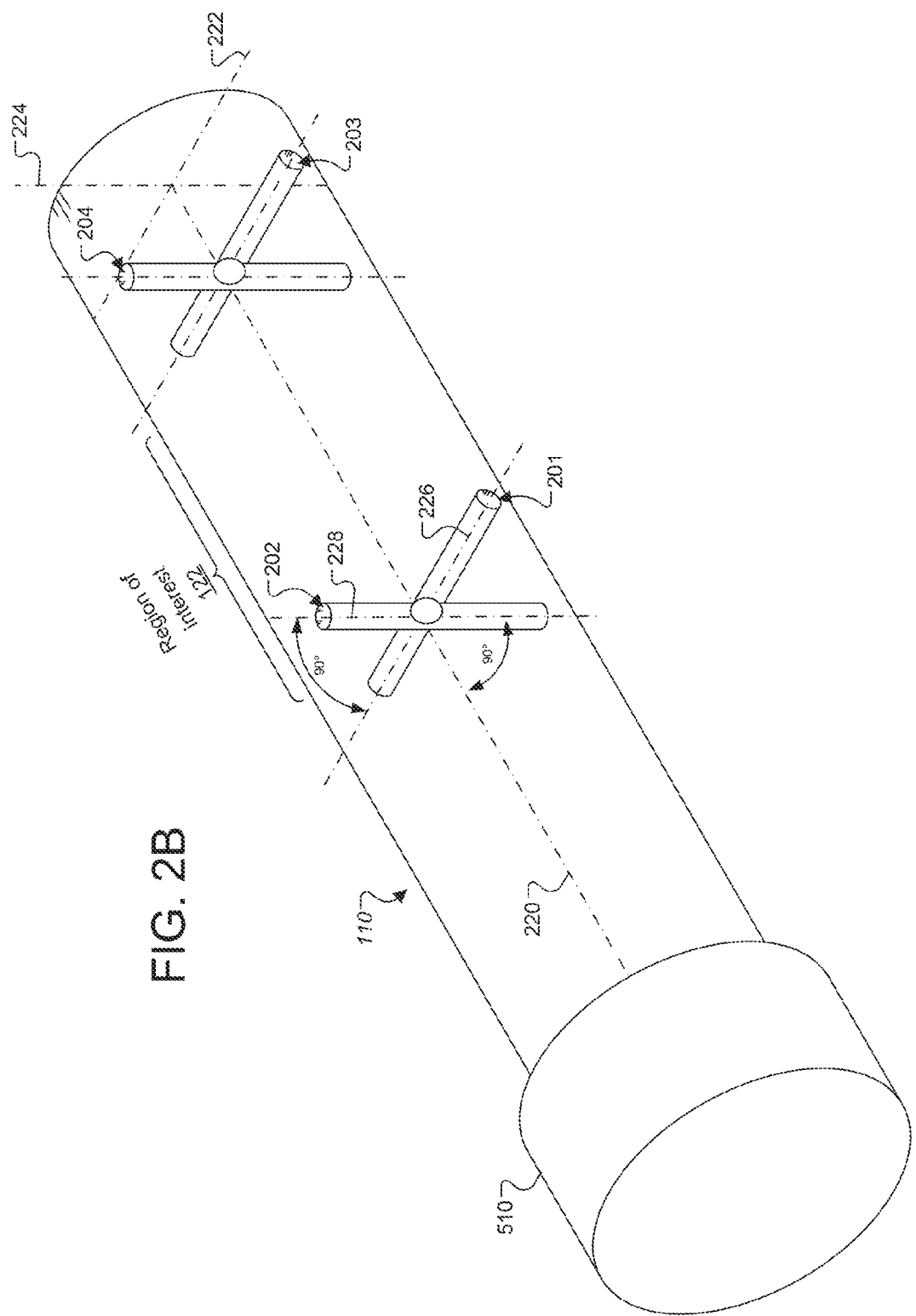

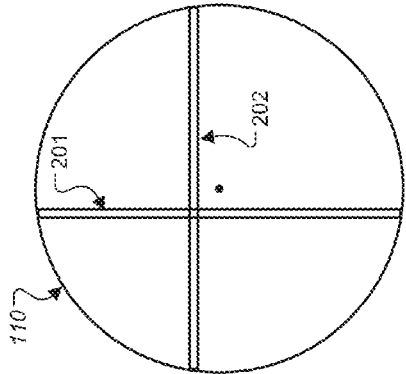
FIG. 2E
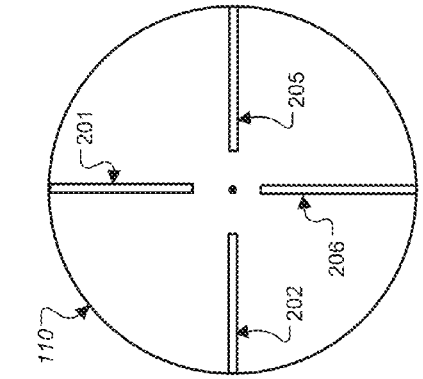
FIG. 2H
FIG. 2D
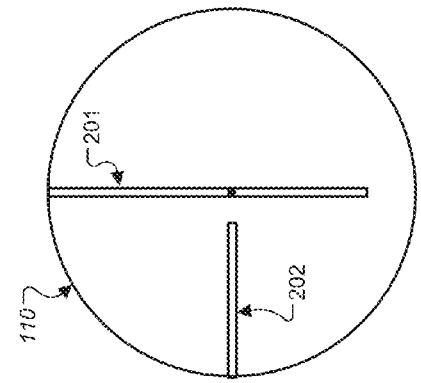
FIG. 2G
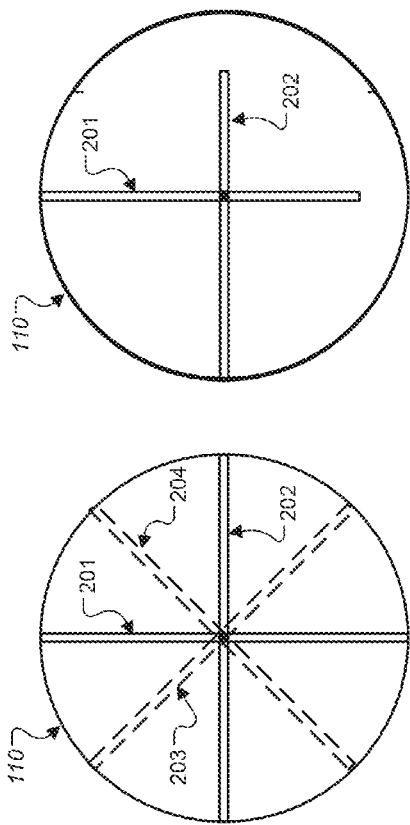
FIG. 2C
FIG. 2F

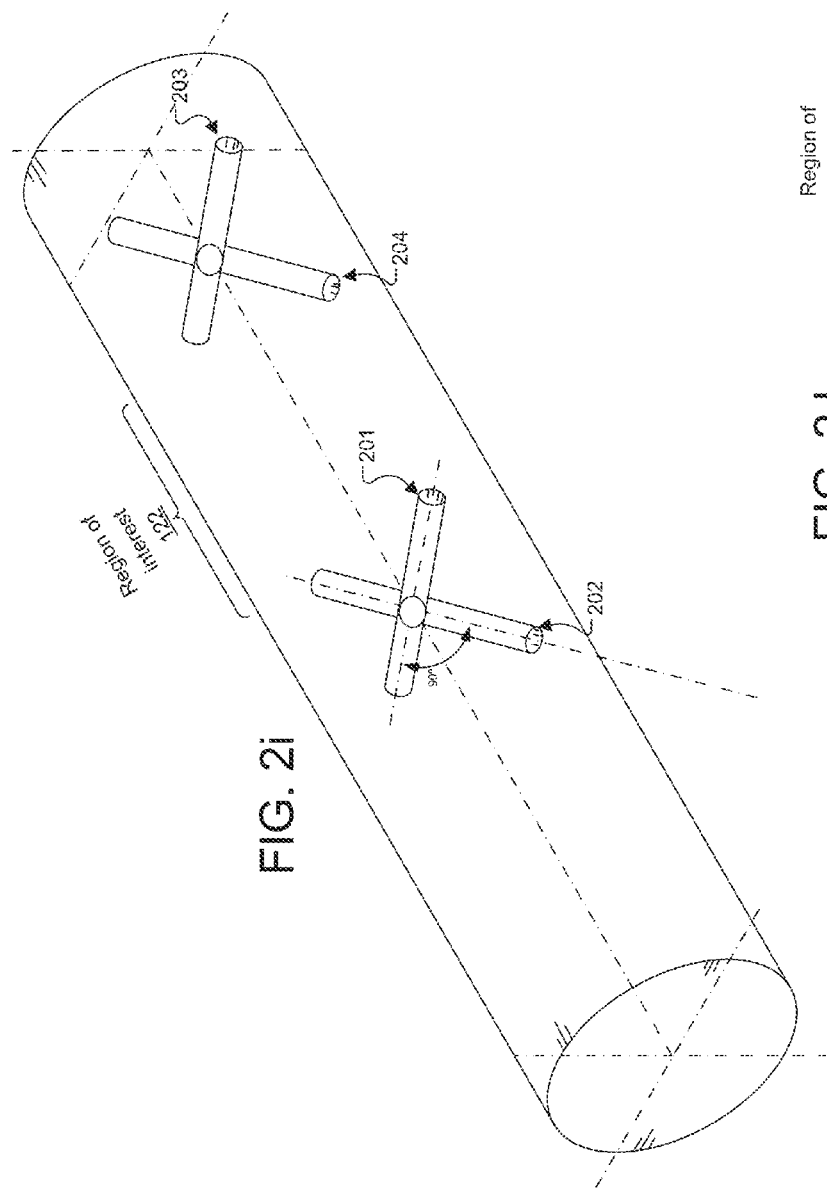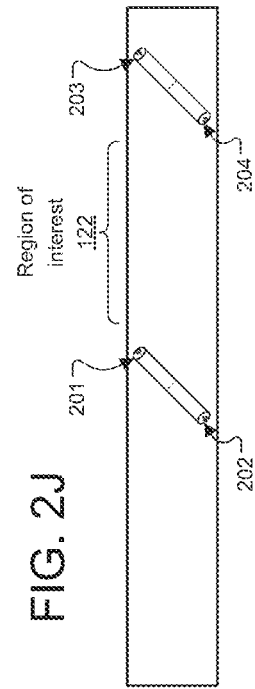

FIDUCIAL FORMATION FOR TEM/STEM TOMOGRAPHY TILT-SERIES ACQUISITION AND ALIGNMENT

This Application claims priority from U.S. Provisional Application 62/196,246, filed Jul. 23, 2015, which is hereby incorporated by reference.

TECHNICAL FIELD OF THE INVENTION

The present invention relates to a process for creating fiducial structures in a sample for use with tomography processes, especially in charged particle microscope tomography.

BACKGROUND OF THE INVENTION

Modern tomography is the process of forming data models of three-dimensional objects by combining 2D projections of the object of interest typically obtained through the use of any kind of penetrating particle or wave. Tomography is a rapidly advancing imaging technology with broad applications in such varied fields such as but not restricted to medicine, dentistry, biology, environmental, toxicology, mineralogy, and electronics. Tomographic processes use various tools, such as x-ray systems, transmission electron microscopes (TEM), scanning transmission electron microscopes (STEM), and/or atom probe microscopes (APM) to obtain various types of information such as, for example, atomic structure and chemical analysis of the sample. A 3D tomography dataset is typically obtained by back projecting a series of 2D images acquired through the sample at different angles, or in the case of an APM by reconstructing a volume from a sequence of field-evaporated atoms striking a position-sensitive detector.

TEMs and STEMs allow observers to see extremely small features, on the order of nanometers, and allow analysis of the internal structure of a sample. For convenience, the reference to TEMs and STEMs will be indicated by the term "S/TEM" and references to preparing a sample for an S/TEM are to be understood to include preparing a sample for viewing in a TEM or a STEM. The sample must be sufficiently thin to allow many of the electrons in the beam to travel though the sample and exit on the opposite side. Thin S/TEM material and electronic samples are often seen as a thin section, referred to as a "lamella," cut from a bulk sample material. Such lamellae are typically less than 100-200 nm thick, but for some applications a lamella must be considerably thinner. In S/TEM tomography, an electron beam is passed through the lamella and images acquired while the microscope stage is incrementally tilted. During this procedure the specimen rotates around an axis set to allow the feature of interest to remain in the field of view. A three-dimensional reconstruction of the original structure is then obtained. As the lamella is tilted, the angle between the beam (optical axis of the microscope) and the lamella surface decreases and the path length of the beam through the specimen increases, limiting the tilt angle than can be used and producing an undesirable "missing wedge effect" in the reconstructed volume. This missing information limits the resolution of the reconstructed volume and produces volumes that look stretch if observed from their side (conventionally along their z axis).

Some recent S/TEM tomography technique use pillar-shaped samples that are nominally cylindrical and contain a region of interest (ROI) desired to be examined by electron tomography. By "pillar" or "pillar-shaped" is meant any tomography sample such that a beam in a plane normal to the longitudinal axis of the pillar can pass through the sample from any direction. A pillar or pillar-shaped sample typically is roughly circularly symmetric (cylindrical or cone shaped). The use of pillar-shaped samples with a rotation holder offers two advantages: they allow a full rotation to eliminate missing wedge artifacts, and they provide a sample with a constant projection thickness at all rotation angles when rotated about the pillar's longitudinal axis (desirable for electron energy-loss spectroscopy (EELS) studies, for example).

In life sciences, techniques of adding fiducials like gold particles to the sample have proven useful to improve the quality of the 3D reconstruction on sectional type samples (mostly because the samples deforms locally under the beam during the acquisition).

In current methods for S/TEM tomography of materials science samples and semiconductor device samples, the alignment of pillar sample tilt-series relies mainly on cross-correlation between pairs of images through the tilt series. The alignment during the reconstruction phase has also been done using Discrete Algebraic Reconstruction Technique (DART) tomography by research groups in Belgium and Germany (IMEC, EMAT, University of Antwerp, IFW Dresden). Also, the current processes of aligning +/−90 degree tilt series from STEM tomography acquired on pillar samples has not become routine yet and is largely conducted manually by the operator, with low repeatability and little dedicated software features for alignment beyond cross-correlation.

SUMMARY OF THE INVENTION

An object of the invention is to improve tomography of pillar-shaped samples.

Provided are methods to create fiducial holes using charged particle beams, and using the fiducial holes to improve the sample positioning, during acquisition, alignment, reconstruction, and visualization of tomography data sets for this type of specimen.

(a) providing a sample in a conical or pillar shape for examination by tomography;

(b) positioning the sample in a charged particle beam system in a first position and directing a charged particle beam at the sample to create a first fiducial, and preferably at least two fiducials. The first one at any orientation and the second one after rotating the pillar-shaped specimen 90 degrees around it longitudinal axis.

(c) after creating the first fiducial, positioning the sample in a microscope for a series of tomographic data acquisitions;

(d) conducting a series of tomographic data acquisitions of the sample with the microscope;

(e) based on the position of the first fiducial in the tomographic data acquisition, aligning data in the tomographic data scans.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a thorough understanding of the present invention, and advantages thereof, reference is now made to the following descriptions taken in conjunction with the accompanying drawings, in which:

FIGS. 2A-B show sequential perspective views of a pillar sample being modified to form fiducial holes according to some embodiments.

FIGS. 2C-H show sample pillars with different arrangements of fiducial holes according to various configurations.

FIG. 2I shows a perspective view of a pillar sample with slanted fiducial holes according to other embodiments.

FIG. 2J shows a longitudinal view of the pillar sample of FIG. 2I.

DETAILED DESCRIPTION OF PREFERRED EMBODIMENTS

Figure 1:
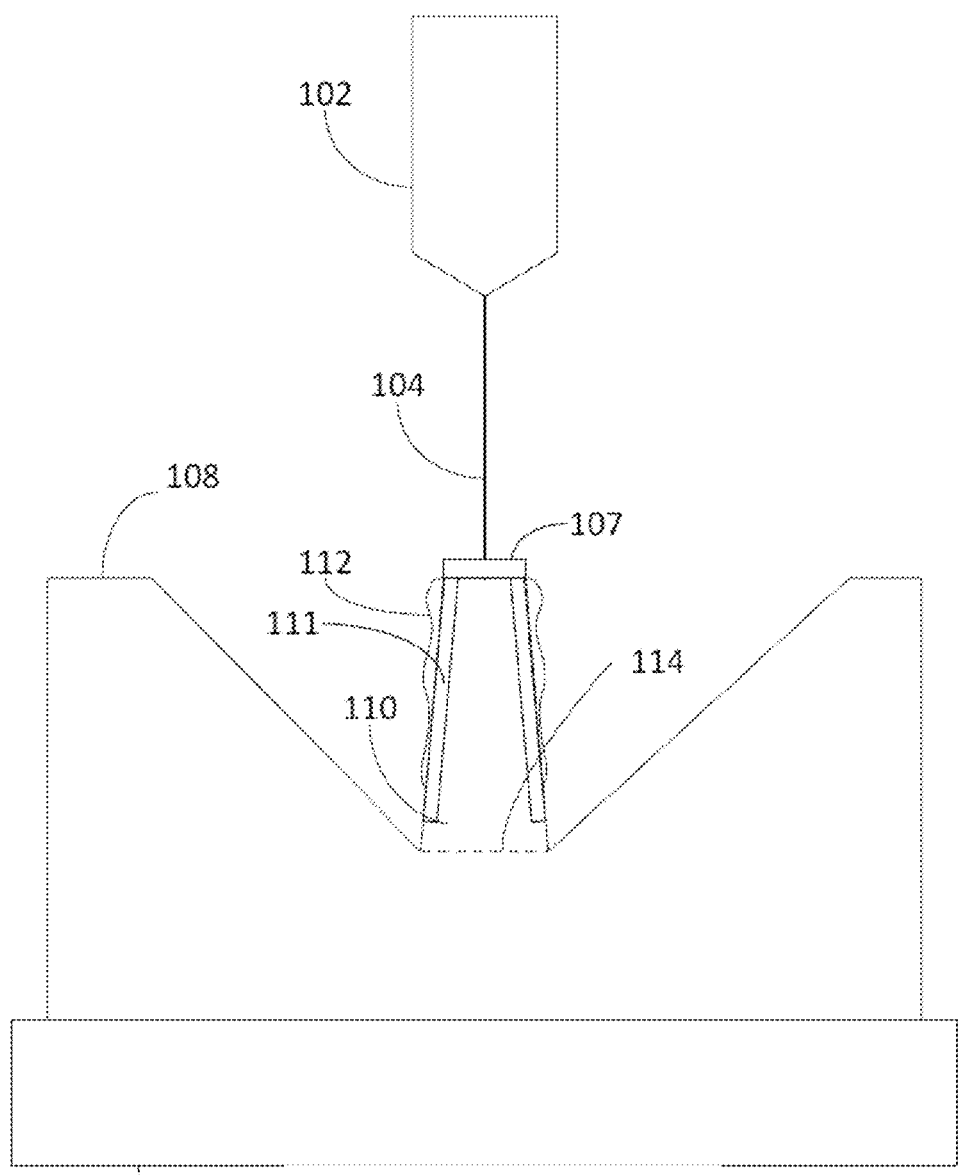
FIG. 1 shows a FIB system in an initial orientation for preparing a sample for TEM analysis from a bulk substrate.

In some embodiments, fiducial holes are created using an ion beam during the process of milling the sample lamella or sample pillar. Other embodiments create in situ fiducial holes with the TEM electron beam prior to acquiring a tomography data series or tilt-series. Preferably two sets of holes are made, but as few as one fiducial hole to very many may be created, with the arrangement of the fiducial holes preferably designed to help either during the tomography process or after aligning the tilt-series before reconstructing it into a 3D volume. The holes may be at right angles to the sample longitudinal axis, or created at other angles. In some versions multiple sets of fiducial holes are made, positioned strategically around a region of interest. The holes preferably pass entirely through the sample but some versions may provide holes to any desired depth.

The fiducial holes may be employed to properly maintain the position of the features of interest during the acquisition, and later to help better align the tilt-series, and improve the accuracy and resolution of the final reconstruction. When operators attempt to acquire a tilt series on a pillar that is not mounted in a perfectly straight manner to the tilt sample holder, the sample rotation causes precession movement which shows up as x, y, and z directional shift because of sample tilt versus the rotational sample holder or tilt sample holder. The fiducial holes according to the invention help correct such problems during tomography acquisition.

Some embodiments form orthogonal sets of fiducial holes by placing the beam in STEM dwell or park mode above or below the features of interest at 0 degrees tilt and 90 degrees tilt, creating beam induced fiducial holes that are orthogonal holes all the way through the pillar sample. Other embodiments form fiducial holes with an ion beam, preferably the ion beam device in which the sample is originally milled, with the holes arranged in orthogonal sets or other desired configurations. Such fiducial holes are employed to track the sample through the tilt series. The fiducial holes are also useful later during the alignment process to improve the quality of the alignment and thus of the final reconstruction. In some embodiments, the operator or the system software identifies the holes to be tracked using tomography feature tracking techniques. Some methods may measure, or provide a precise size, for the fiducial hole cross-section at different depths, enabling better 3D metrology to be conducted on samples.

Creating and using fiducial holes according to the invention preferably does not require significant changes to specific preparation protocols for mineral or semiconductor samples, and preferably does not disturb the structures under investigation prior to observing them in the TEM. Further, the techniques herein may be applied to improve tomography characteristics without using traditional electron microscopy fiducials such as gold particles, and without other wet contaminants added to the sample. Fiducial holes as described herein may also be filled with desired materials or particles to enhance accuracy or metrology, for example. In certain cases, charged particle created fiducial holes may be applied with tomography samples in other scientific fields, such as biological samples. During the acquisition of a tilt-series, structures observed and present through the pillar may be very repetitive (especially for electronic samples) and depending on the cut orientation chosen during the FIB milling of the sample, it may be difficult using conventional techniques to keep the feature of interest in the center of the field of view as the sample tilts. Creating distinct fiducials according to the techniques herein helps alleviate such problems by improving the quality of the acquisitions performed on such pillar samples, as well as the alignment of data series.

In accordance with some embodiments, a pillar, cone, or other sample portion suitable for S/TEM analysis is prepared for tomography analysis using a focused ion beam or other method. A sample containing a region of interest (ROI) is cut from a bulk material using FIB techniques. One known example of cutting a sample from a bulk material is shown in FIG. 1, and further described in U.S. patent application Ser. No. 14/627,770, filed Feb. 20, 2015, and titled "Fabrication of a Malleable Lamella for Correlative Atomic-Resolution Tomographic Analyses," which application claims priority to U.S. Provisional App. 61/948,516, filed Mar. 5, 2014, the contents of which applications are both hereby incorporated by reference.

Referring to FIG. 1, the bulk sample material 108 is loaded onto sample stage 106 of the tool, which is preferably a dual beam FIB/STEM system. The stage 106 may provide a plurality of motion axes, including translation, rotation, and tilting such that an optimal orientation of the sample may be achieved at each step of the lamella formation process. A FIB column 102 is shown in an orientation for performing initial milling on a bulk sample material to create a sample pillar for S/TEM analysis. In this embodiment, substrate 108 is oriented so that its top surface is perpendicular to focused ion beam 104 emitted from the FIB column 102. Optionally, a protective layer 107 is deposited over the region of interest, for example, by beam-induced deposition of platinum, tungsten, or silicon dioxide or Carbon to protect the region of interest and to reduce ion milling artifacts. Alternatively or in addition to the beam-induced deposition previously described, a protective capping layer could be deposited on the surface of the sample prior to loading the sample into the focused ion beam system. Most of the coarse ion beam milling done to create pillar 110 is performed with substrate 108 and FIB column 102 in this orientation. Due to the focusing (i.e., a convergent conical shape) and the path of ion beam 104, this perpendicular milling causes pillar 110 to be tapered from top to bottom. That is, pillar 110 is thinner at the top than it is at the bottom. In this embodiment, pillar 110 remains securely attached to substrate 108 at boundary 114. For the case where pillar 110 is formed in a substrate larger than a few tens of micrometers in width or length, the pillar 110 must be removed from substrate 108 and thinned to electron transparency before it can be used in the S/TEM. In addition, material removed from substrate 108 while milling with ion beam 104 in the vertical orientation may be re-deposited onto the face of pillar 110, forming an undesirable layer 112 of foreign material. Likewise, the use of a high-energy focused ion beam to form a pillar in the substrate results in a thin intermixed layer of elements 111 at the FIB milled-surface materials and the species used for ion milling, typically gallium, argon, or xenon. The presence of layers 111 and 112 reduces the quality of the S/TEM analysis and must be removed or polished away before pillar 110 can be used with the S/TEM.

The FIB system may be repositioned in a tilted orientation for post-processing a sample pillar using over-tilting, polishing, and/or undercutting. Over-tilting is the process of removing the taper from the sides of pillar 110 to make the faces of pillar 110 substantially parallel. Polishing is the process of removing layer(s) 111 and 112 from pillar 110 that accumulated on pillar 110 from the previous initial milling. Undercutting is the process of partially or fully detaching pillar 110 from substrate 108 at or near boundary 114. Either sample stage 106 or FIB column 102 is rotated an angle about the long axis of pillar 110. That is, either sample stage 106 or FIB column 102 is rotated an angle 116 relative to a plane defined by the long axis of pillar 110 and the normal to the top surface of substrate 108. Put another way, sample stage 106 or FIB column 102 is rotated about an axis that is perpendicular to the sheet of FIG. 1 and located within the cross-section of pillar 110 shown in FIG. 1, preferably near the center of the cross-section of pillar 110. While a cylindrical pillar shaped samples is depicted being created, this is not limiting and other shapes may be used. Preferred alternative shapes are symmetrical about a longitudinal axis, such as cones or tapered pillars. Other shapes such as traditional lamella shapes, where the size and shape of the lamella allows for acquiring a tilt series of some type, may be employed in different versions. Further, while a traditional rectangular lamella does not allow acquisition of full a +/−90 degrees tilt-series, in some applications an extremely thin rectangular lamella may be used, allowing for acquisition of a +/−85 degrees tilt-series. It is noted that while a full a +/−90 degrees tilt-series is preferred for accuracy, the techniques herein may be employed to advantage with systems that use less than a full tilt series. For example, +/−85 degrees, +/−80 degrees, +/−75 degrees, +/−70 degrees, +/−65 degrees, or +/−60 degrees, may be used, and the techniques herein may be employed to advantage in almost any functioning tomography data scan scenario where traditional fiducials are not desired and holes can be created. In fact, the improved accuracy provided by the techniques herein is beneficial to scans with a limited range such as +/−60 degrees.

In order to finish forming the desired sample shape for tomography, or after such shape is formed, the sample is transferred to a tilt sample holder or rotational sample holder using a motorized nanomanipulator and welded to the mount using an ion or electron beam-induced deposition process, or using a mechanical mechanism, or adhesive material, in a known manner. The sample pillar 110 may be formed by any known conventional technique, including but not limited to mechanical shaping, and broad beam ion milling, in addition to the aforementioned focused ion beam milling methods. The sample may be coated by ion beam deposition or other techniques for certain applications. Generally the processes described below will employ a series of sequential annular mills and to shape the lamella into a cylindrical-shaped pillar specimen 110 in a suitable manner. Other versions may shape the lamella 120 with a needle shape tip, with a region of interest positioned toward the tip of the needle. Any suitable FIB mill process may be utilized to form the needle-shaped sample. One example is shown and disclosed in U.S. Pat. No. 7,442,924 to Giannuzzi et al for "Repetitive Circumferential Milling for Sample Preparation," assigned to the assignee of the present invention, which is fully incorporated herein by reference.

FIGS. 2A-B show sequential perspective views of a sample pillar 110 being modified to form fiducial holes according to some embodiments. In FIG. 2A, the depicted sample pillar 110 is shown positioned or held with its longitudinal axis 220 perpendicular to a charged particle beam, which may be an ion beam or an electron beam such as a TEM electron beam in some versions. According to methods discussed below, as depicted the charged particle beam is directed along the central axis 226 of the desired fiducial hole to create the first fiducial hole 201. In FIG. 2B, sample 110 is shown attached to a rotational sample holder 510 and rotated 90° with cross axis 222, previously depicted oriented vertically, now oriented horizontally, and the pervious horizontal cross axis 224 now oriented vertically with respect to the charged particle beam path direction, which is vertical in the figures. Another set of fiducial holes, 203 and 204, are shown formed at the opposing end of the region of interest 122. Preferred processes for forming the depicted fiducial holes 201-204 will now be described further with reference to the process flowcharts of FIGS. 3A-B as well as FIGS. 2A-B. It is noted that while the depicted pillar is shown idealized as a cylinder, in practice pillars often have uneven or rough surfaces, and are often needle shaped with a rounded end rather than perfectly cylindrical. As such, the phrases pillar, pillar-shaped, cone, or conical as used herein should not be limited to perfect cylinders or cones unless otherwise specified, and should not be limited to smoothly-surfaced shapes. Further, while pillars, needles, or cone samples are desired that are rotationally symmetrical about a central axis, such a term should not be interpreted as required perfect symmetry, because unevenness, local asymmetry, roughness, and skew are often present in sample pillars and other shapes.

Figure 3A:
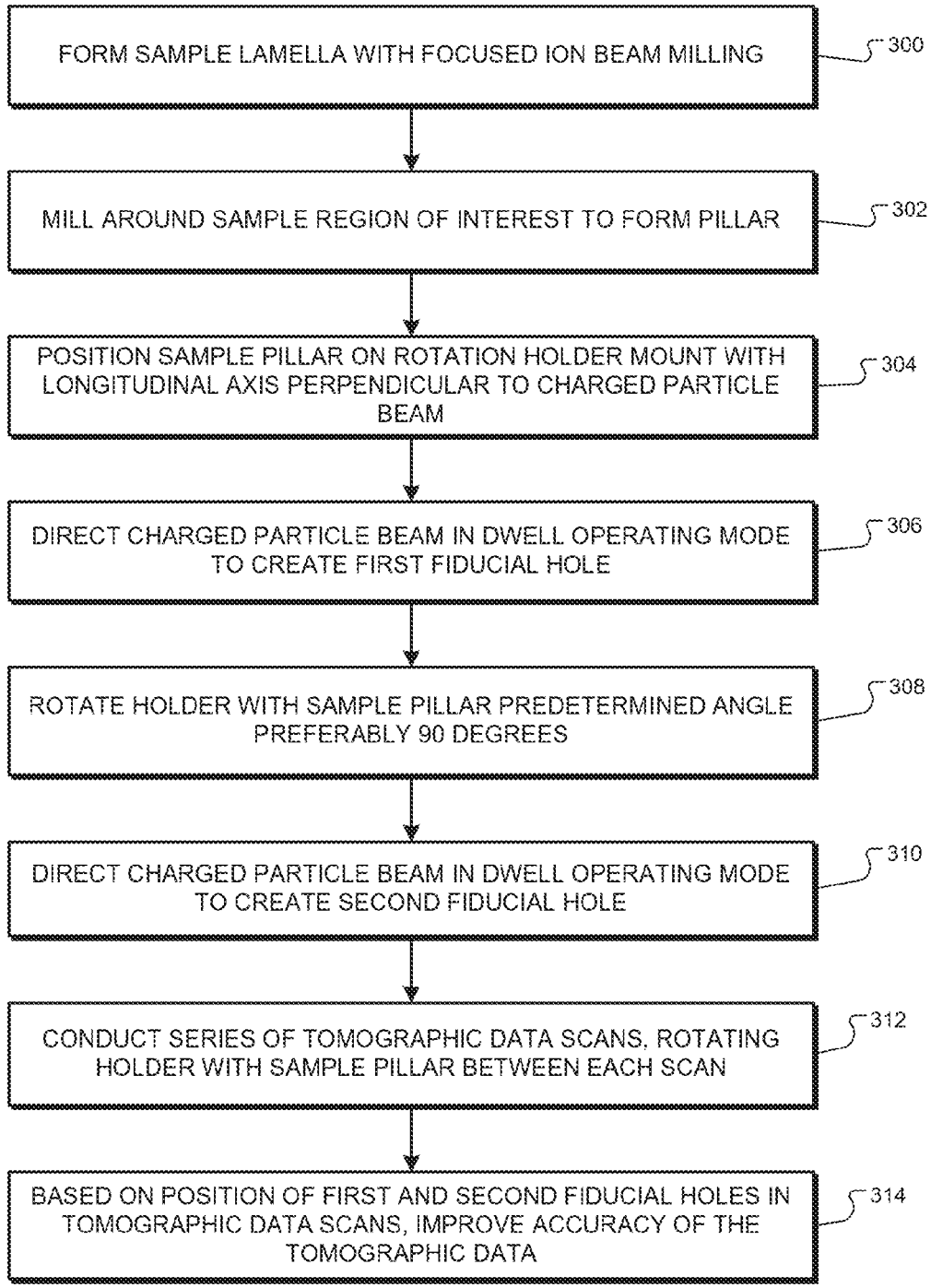
FIG. 3A is a flowchart of a process of creating and employing fiducial holes according to some embodiments.

FIG. 3A is a flowchart of a process of creating and employing fiducial holes according to some embodiments which create fiducial holes in situ in the sample mount in which they will be examined. Referring to FIG. 3A, the process begins at block 300 where a lamella is formed in the sample, preferably with focused ion beam milling as discussed in the example of FIG. 1. Next at block 302, the process mills around a sample region of interest to form a pillar holding within it the region of interest to be examined. The process of forming sample pillars is known and may be conducted by suitable methods for the particular sample type involved. Before or during the sample pillar's formation, the process at block 304 transfers the pillar to a tomography holder or rotating mount, which may be accomplished by known methods such as ion beam welding the pillar to a nanomanipulator and transferring it, or if available ion beam welding the pillar directly to the tomography holder. The sample pillar 110 is cut or otherwise removed from the substrate 108 at some point in this process. The process of mounting sample pillars and lamellas to the tomography holders or tilt holders is known and will not be further discussed here. Block 304 includes positioning the sample pillar 110 with the longitudinal axis 220 perpendicular to a charged particle beam. Other versions may provide for some angle offset from perpendicular. In some versions, the charged particle beam may be the same beam that will be used for tomographic scans, but in other versions such as the versions of FIG. 3B, an ion beam creates the fiducial holes. Positioning the sample at block 304 may involve moving the sample from an ion beam milling device to a TEM, while other embodiments may employ a dual beam device including an ion beam and a TEM and merely reposition sample pillar 110 within a sample chamber at block 304.

At block 306, the process directs a charged particle beam in a dwell mode onto the sample to create the first fiducial hole 201. If a TEM electron beam is used set in dwell mode, the beam energy is preferably set to the highest setting such as 200 KeV, but different sample types may use different beam energies. The beam current may also be adjusted depending on the sample type, but for preferred silicon semiconductor samples the beam current may be set to 5 nA. The beam is directed onto the sample pillar 110 long enough to create a hole to the desired depth, or through the entire thickness of the pillar. Penetrating the entire thickness typically takes around 20 seconds to 1 minute but may vary depending on many factors including pillar thickness, which may vary from thin pillars (15 nm and under) to thicker pillars or other lamellas that may be on the order of 200 nm thick or thicker around the region of interest. The hole may vary in size depending on the application and the hole formation technique as further discussed below. The process at block 306 may optionally create another hole at the same orientation, but a different longitudinal position along the pillar, such as the first and third holes 201 and 203 depicted on either side of the region of interest in FIG. 2B. If such additional hole is created, the sample pillar position may be adjusted longitudinally at this step, or may be rotated as depicted at block 308 to create the second fiducial hole 202, and then adjusted longitudinally and the steps repeated to create third and fourth holes 203 and 204. As shown, the holes are preferably 90° of rotation apart and pass through a common plane (that is, they are at the same longitudinal position along the pillar), but both of these factors may vary in some embodiments. Further, while cylindrical holes are depicted, actual holes are often not even approximately cylindrical, instead having a larger diameter near the surface, or near the surface upon which the charged particle beam is applied to form the hole. Holes formed according to the processes herein also often have roughness and irregularity in the hole interior walls.

After rotation, the process at block 310 creates the second fiducial hole similarly to the first. The holes may differ in depth, be of the same depth, or pass entirely through the width of the pillar 110 or other lamella to be examined. Different sets of holes may be created, including holes at an angle not perpendicular to the sample pillar longitudinal axis, such as those shown in FIGS. 2I and 2J, for example. In some versions, only one hole may be created at a desired location and angle to both the sample pillar longitudinal axis 220 and the cross axes 222 and 224.

With the set of fiducial holes completed, preferably two holes, or two sets of two holes each for a total of four holes, the process goes to block 312 where it conducts a series of tomographic data acquisitions, rotating the holder with the sample pillar 110 between each consecutive acquisition. The rotation is preferably about a defined axis such as sample pillar longitudinal axis 220, however this is not limiting, and end-over-end rotation may be used, as well as multi-axis rotation, usually acquired in sets rotating first about a first desired axis, and then about a second. The scans are preferably conducted with a TEM, but may be conducted in some circumstances with a STEM. Because TEM-level tomographic scans are known in the art they will not be further described here.

After or during the series of scans, at block 314 the process uses the position of the first and second fiducial holes to improve the sample positioning, acquisition, alignment, reconstruction, or visualization of tomography data sets as further described below. Such improvement can be made in many parts of the tomography processes, but is especially useful in improving alignment by tilt-series improving on the reliability of the cross correlation during the reconstruction process, especially when repetitive structures are present in the region of interest. It is noted that while first and second fiducial holes are described in the flowcharts herein, various embodiments of the invention may employ more of fewer fiducial holes in any of the described processes. For example, one preferred version uses four fiducial holes arranged as depicted in FIG. 2B. Other versions may use more fiducial holes or only one hole. The processes herein further enable placement of a fiducial, in the form of a hole created by a charged particle beam, across a location where typical TEM fiducials such as gold spheres could not be placed—across the interior of the sample pillar. This is especially beneficial for samples such as silicon or other semiconductors, which otherwise provide little opportunity for fiducial placement at the TEM level.

Figure 3B:
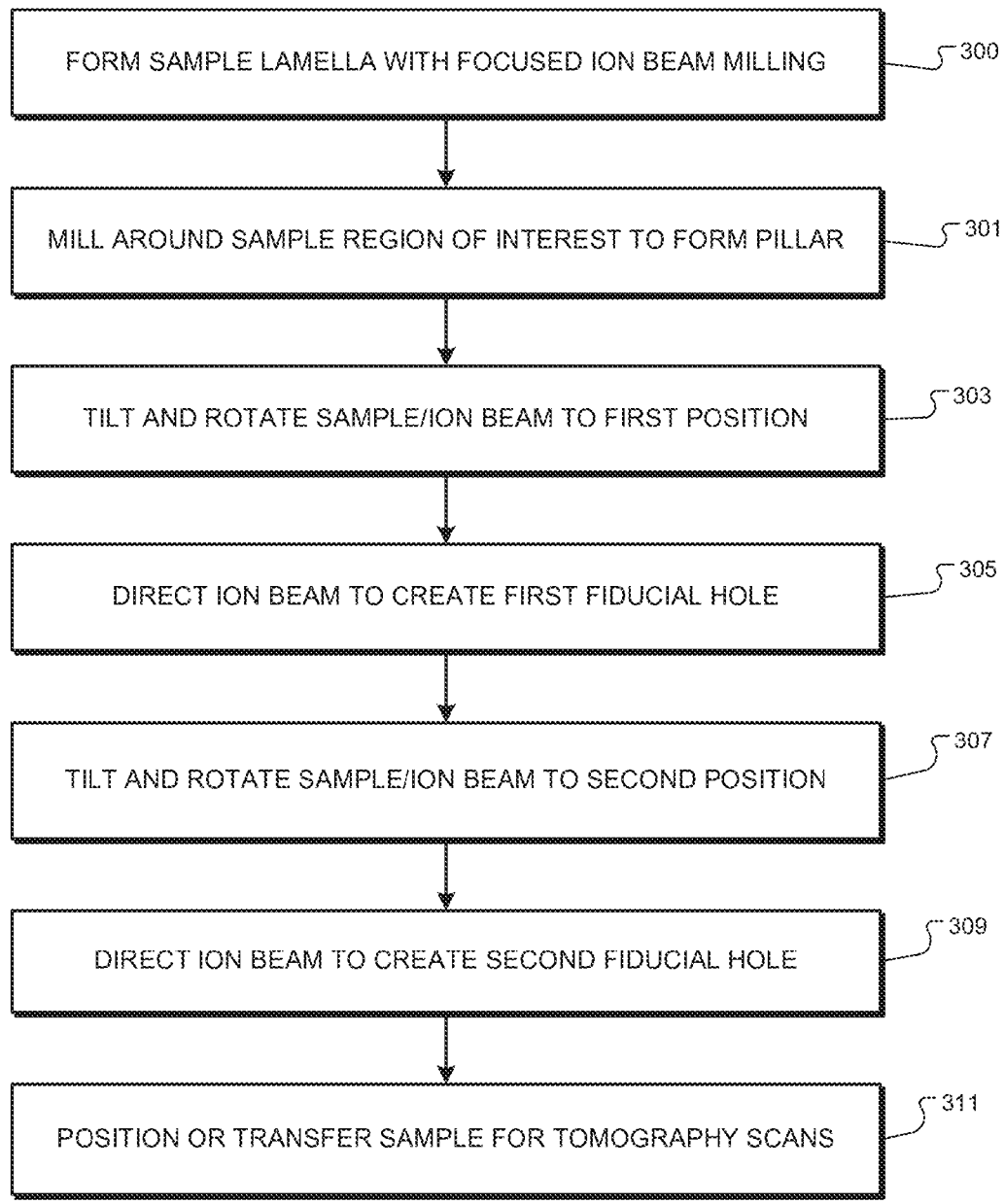
FIG. 3B is a flowchart of a process of creating fiducial holes using an ion beam according to other embodiments.

FIG. 3B is a flowchart of a process of creating fiducial holes using an ion beam according to other embodiments, which create the fiducial holes with the ion beam device in which the sample pillar or other lamella is milled. The process like the previous process with the ion beam milling a lamella in the sample at block 300. Next at block 301, the process mills around the sample region of interest to form a sample pillar, cone, needle, or other desired shape. Next at block 303, the process prepares to create the fiducials holes with the ion beam, by tilting the sample to a first position relative to the beam. In some ion beam devices the beam position may be tilted as well. In some embodiments, this process block will involve removing the sample pillar 110 from the sample substrate and welding or fixing it to a nanomanipulator or other tool or tilt sample holder. In other versions, the sample pillar 110 still attached to substrate 108 is repositioned relative to the ion beam path 104 to create the desired position and orientation (such a process may be used, for example, when fiducial holes that are not perpendicular to the sample pillar longitudinal axis are desired).

Next at block 305 the ion beam is directed onto the sample pillar 110 to create the first fiducial hole 201. The milling may be done according to suitable methods for the sample material, with or without gas. Preferably the first hole is formed passing through the sample, but other fiducial hole depths may be used, and the ion beam is deactivated or blanked after the desired hole is achieved. As in the process of FIG. 3A, further fiducial holes such as hole 203 may be created at the same rotational angle if desired before rotation, or the process may proceed directly to block 307 where it rotates the sample to a desired second position to create second fiducial hole 202. At block 309, the process directs the ion beam at the sample similarly to produce the second fiducial hole 202. Other fiducial holes may be formed after this at other longitudinal positions, preferably at an opposite side of the region of interest from hole 202, such as hole 204 of FIG. 2B, for example. Next the process positions or transfers the sample for the tomography tilt-series acquisition process, which proceeds and described herein employing the fiducial holes to improve the sample positioning, acquisition, alignment, reconstruction, or visualization of tomography data sets.

It is noted that if large holes are desired for larger patterns, the ion beam of the depicted process may be moved in a small pattern to create a hole larger than the beam width, or the beam width may be adjusted. In some ion beam devices, the fiducial hole formed has a larger diameter at the surface, even with the beam in dwell mode. The process of FIG. 3A may be similarly modified for a larger desired hole width. The width of the holes may be measured or characterized for a particular sample type by prior experimentation, and then employed to improve 3D metrology in the tomography process. Further, while the example processes discussed herein employ the fiducial holes in an empty state, the holes may be filled with a desired material or with fiducial markers such as gold spheres of a known size to assist in metrology, for example. Such a process would include steps of placing fiducial markers of a known size into the fiducial holes.

Because the finished holes may be used for both positioning the sample accurately for tomographic scan sequences, and for improved processing of the acquired data, the number and position of holes is selected according to various considerations. FIGS. 2C-H show sample pillars with different arrangements of fiducial holes according to various configurations, in order to provide non-limiting examples of how fiducial holes may be used according to various methods of the invention. Referring now to other fiducial hole configurations, different embodiments of the invention may be many different configurations of holes, depending on various factors such as the shape and size of the sample to be examined, the shape and size of the region of interest, the scannable area size of the tomography scanning device, the resolution desired, and the particular materials involved, to list a non-limiting set of factors which may be considered in determining how many holes may be formed by the processes herein, and what configuration such holes will be provided.

FIG. 2C shows a projection cross sectional view taken at the plane of fiducial holes 201 and 202. This is a preferred configuration of fiducial holes which has all the way through the diameter of the sample pillar 110. The dark dot in the middle of the figures merely indicates the center of the depicted circular cross-section. In this version, the second set of holes 203 and 204 are formed at a different longitudinal location from fiducial holes 201 and 202, such as the longitudinal locations depicted in FIG. 2B for the different sets of fiducial holes. In the version of FIG. 2B, fiducial holes 203 and 204 are rotationally aligned with holes 201 and 202. However, in the example of FIG. 2C, fiducial holes 203 and 204 are formed rotationally offset from holes 201 and 202, preferably 45° offset as depicted by holes 203 and 204 shown in dotted lines as they are projected onto the plane to be compared with holes 201 and 202. Such a technique may be used to form angularly offset sets of fiducial holes at different locations along a sample pillar 110 in any of the various configurations described herein, and other configurations not specifically given as examples.

FIG. 2D shows an alternative embodiment, in which holes 201 and 202 did not completely penetrate sample pillar 110 across its entire diameter. Instead, they pass more than halfway through the diameter, but not entirely through to the opposite edge of the sample pillar 110. It is desired in most embodiments to have the fiducial holes penetrate at least to the center of the pillar, in order to provide reference data in the tomographic scan data to accurately align features at the center of the pillar, which usually contains details of interest in the region of interest 122.

FIG. 2E shows another example embodiment, not preferred, in which the fiducial holes do not pass through the center of the pillar 110, but instead are offset by a determined amount, which may be different or maybe the same offset. It is noted that offset fiducial holes in some embodiments may also not penetrate all the way to the opposing edge of the sample pillar 110.

FIG. 2F shows another cross-sectional view in which fiducial holes 201 and 202 do not penetrate all the way to the center of the pillar 110, but do get close to the center, such as a depth of 80% or 90% of the radial size of the pillar, for example. The fiducial holes may penetrate to any desired depth and different holes may have different depths, such as one at 80% and one at 90%, or one at 85% and one at 95%. Such a configuration may be desirable, for example, when fiducial holes are used positioned longitudinally inside the region of interest in a thick sample pillar for example in which the region of interest is much smaller than the pillar thickness and position in the center of the pillar. Further, such a configuration may help improve cross-correlation correction of individual acquisitions by providing a gap visible in the center of some micrographs.

FIG. 2G shows another cross-sectional view in which fiducial hole 201 penetrates more than halfway through the sample pillar 110, while fiducial hole 202 penetrates less than halfway. FIG. 2H shows another cross-sectional view in which the set of holes at a particular longitudinal location includes four fiducial holes, each offset a 90° from the adjacent holes, with extra holes 205 and 206 being created by further rotating the sample pillar 110 and directing the beam, whether ion or other charged particle beam, to create a new fiducial hole. While four fiducial holes are shown in this embodiment, other versions may have more fiducial holes such as 5, 6, 7, or 8 at the same longitudinal position on sample pillar 110. Furthermore, while the fiducial holes are shown as penetrating in this embodiment most of the way to the center of the device, this is not limiting and fiducial hole configurations as discussed may provide for holes at any depth including much shallower or deep holes such as holes that are 10%, 20%, 30%, 40%, 50%, 60%, 70%, 80% or, 90%, for example, of a radius or a diameter in any of the embodiments described herein. A fiducial hole of a targeted depth may be created by first measuring a penetration rate of the beam on the sample, and then calculating from that rate the length of time to apply the beam on the sample for the desired depth.

FIG. 2I shows a perspective view of a pillar sample with slanted fiducial holes according to other embodiments. FIG. 2J shows a longitudinal view of the pillar sample of FIG. 2I. In this version, the fiducial holes are not drilled perpendicular to the longitudinal axis of the sample pillar, or other sample such as a cone, needle, traditional lamella, wedge, or any shape of sample for which a tomographic acquisition is desired. Fiducial holes 201 and 202 as depicted in the figure are created at an angle from the perpendicular plane example used in FIG. 2B, the angle more easily seen in the side view of FIG. 2A. Again in this embodiment, two sets of fiducial holes are provided at either end of the region of interest 122, but this is not limiting more or fewer sets may be employed. The configuration depicted here they be useful for example when holes are desired to be formed while the sample still attached to the substrate in a tilt sample holder such as the configuration depicted in FIG. 1. As such, the sample holder and the ion beam may be tilted as far as possible to allow the beam to penetrate the side of the sample pillar 110, but the configuration may not allow a direct perpendicular approach because the beam would be blocked by the presence of the substrate in which the sample pillar has been formed. In such cases, as steep an angle as possible is desired, that is as close to 90° as possible is desired. Other versions may use shallower or steeper angle from the longitudinal axis, for example 30°, 40°, 45°, 50°, 60°, 70°, 80°, or any angle from parallel to the longitudinal axis to perpendicular. In some rare cases, a fiducial hole may be desired that is along the longitudinal axis, or parallel to the longitudinal axis but offset toward a selected side of the sample pillar. Further, such a longitudinal fiducial hole may be employed in combination with other slanted or perpendicular holes as described herein. It should be understood that while several different configurations of fiducial holes have been discussed, this is not limiting and other fiducial hole arrangements may be used in the processes described herein.

Figure 3C:
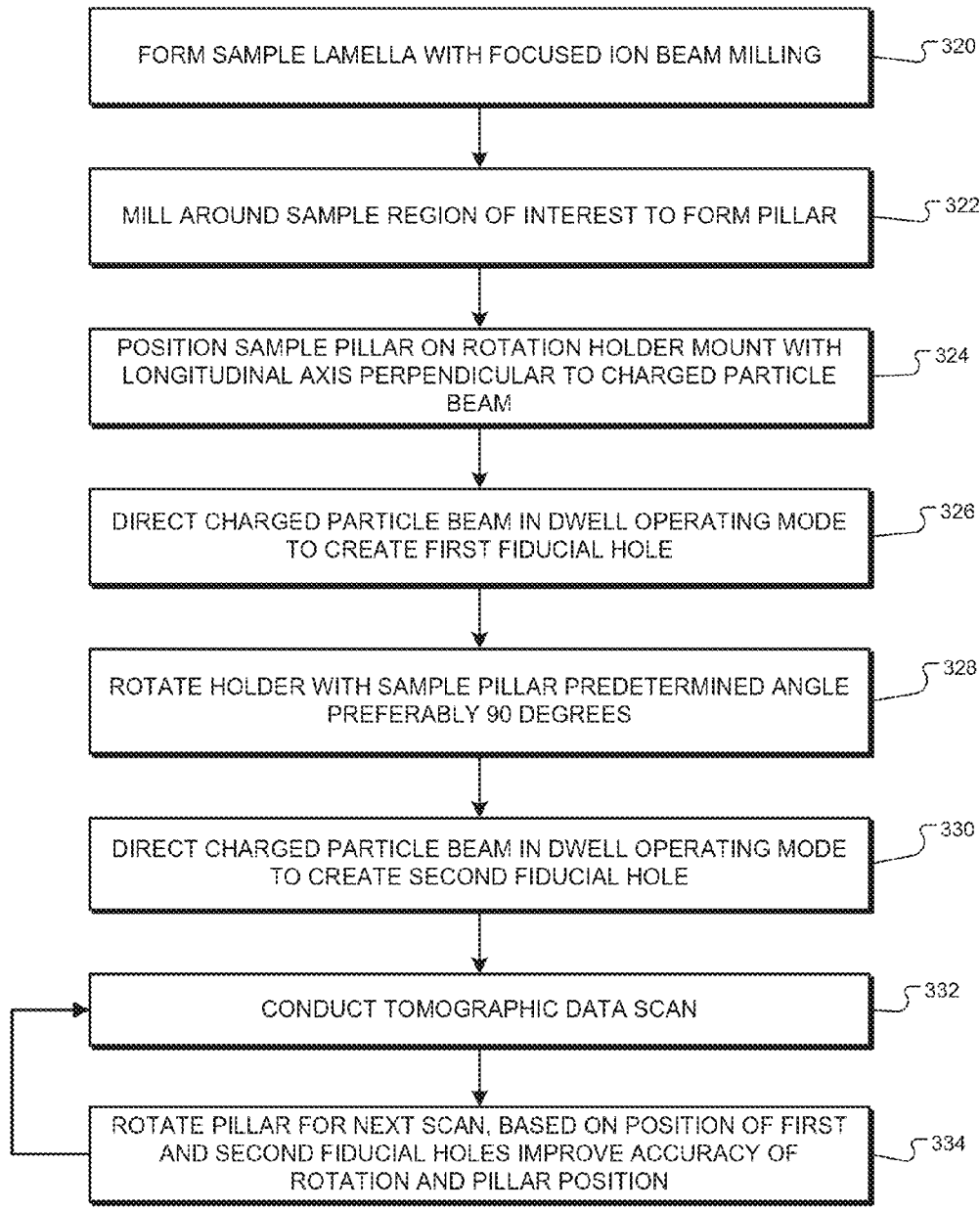
FIG. 3C is a flowchart of a process for creating and using fiducial holes to improve sample pillar position accuracy for a series of tomographic data acquisitions.

FIG. 3C is a flowchart of a process for creating and using fiducial holes to improve sample pillar position accuracy for a series of tomographic data acquisitions. The process begins similarly to the previous two processes, by forming a lamella in the sample using focused ion beam milling at block 320. Blocks 320 through 330 proceed identically to the steps for creating the fiducial holes as described with respect to FIG. 3A. The process of FIG. 3B may be employed instead. Next, at block 332, the process positions the sample for a sequence of high resolution imaging, preferably in a TEM as already described. The process conducts a single scan in the series at block 332 and saves the resulting scan data to memory. Next, at block 334, the process rotates the pillar for the next acquisition by an angular rotation of the tilt sample holder or rotational sample holder employed, the amount of angular rotation determined by the desired angle interval between acquisitions the particular process used. Block 334 also adjusts the position of the sample pillar following the rotation based on the observed position of at least one of the 1st and 2nd fiducial holes. Such adjustment require a tilt sample holder moveable in more directions than merely the rotational direction, and may correct precession movement, over rotation, under rotation, or other undesired positional inaccuracies to place the region of interest in a desired location for the next scan in the tomographic scan series, as further described below with respect to FIG. 4B. After block 334, the process returns to block 332 and conducts the next scan and sequence. These steps are repeated, using the 1st and 2nd potential holes to more accurately position the sample pillar 110 at each successive rotational movement. Different systems may enable the operator or the visual observation system employed to position the sample to view only a narrow angular view of the sample pillar, which might in some cases only enable viewing of one hole opening any time. Preferably, the viewing angle available will show at least 90° of view along the curved surface of the sample pillar 110, meaning that at least one hole opening will always be visible for the adjustment process at block 334. For systems in which a smaller observational view is provided, more than four hole openings may be needed in order to accurately track the position of the pillar after each rotation. For example, some versions may include six fiducial holes at equal angular intervals around the circumference of the sample pillar 110, which penetrate nearly halfway radially into the sample pillar 110, such as 30% or 40% through the entire width of the sample pillar. It is further noted, that while visual or image observation of the sample exterior is used in this example, other versions may use x-rays or preliminary lower resolution scan, or even a full resolution tomographic scan employed only for positioning purposes to correct positional errors after each successive rotation at block 334.

Figure 3D:
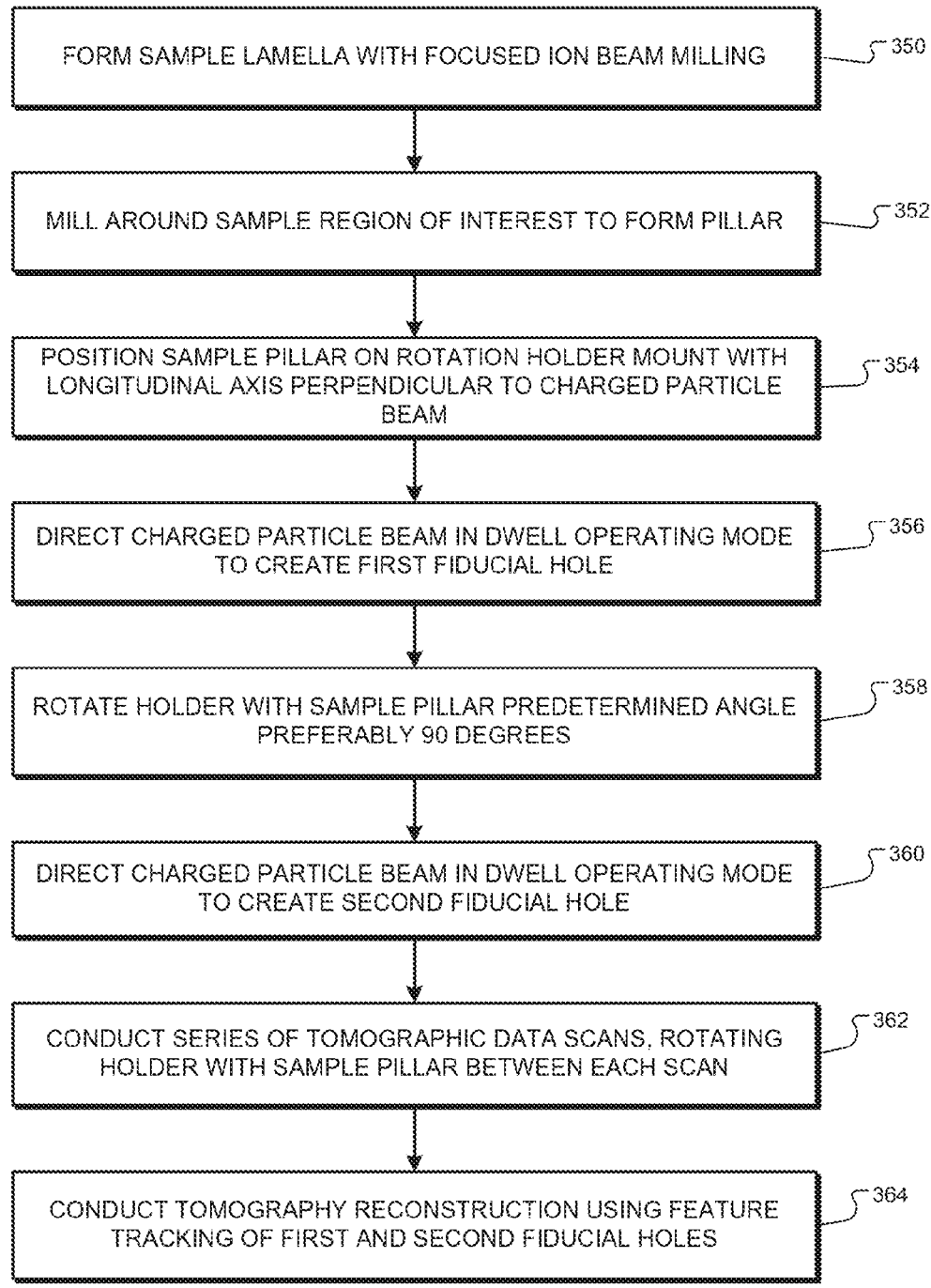
FIG. 3D is a flowchart of a process for creating and using fiducial holes to improve reconstruction for a series of tomographic data acquisitions.

FIG. 3D is a flowchart of a process for creating and using fiducial holes to improve reconstruction for a series of tomographic data acquisitions. The depicted process is also conducted similarly to the process of FIG. 3A from blocks 350 to 360, which form the sample pillar 110 and the fiducial holes. The fiducial holes may instead be formed by the process of FIG. 3B, or other suitable processes. When the fiducial holes are formed, the process goes to block 362, where it conducts a series of tomographic data acquisitions of the sample pillar. The series of scans may include employing the fiducials holes to correct the sample position before the first scan and after each rotation or repositioning, which is also known as the tracking process, as described with respect to FIG. 3C. When the tomographic data scans are complete, the process goes to block 364, where it conducts the tomography reconstruction tilt-series, reconstructing a 3D volume of the data acquired. In order to obtain the best reconstruction, feature tracking techniques are employed using the fiducial holes as the tracked features, thereby enhancing the accuracy of the alignment process. The feature tracking may occur in cross-correlation alignment of the scans before reconstruction, and may also occur as part of the reconstruction and visualization, as further described below.

Figure 4A:
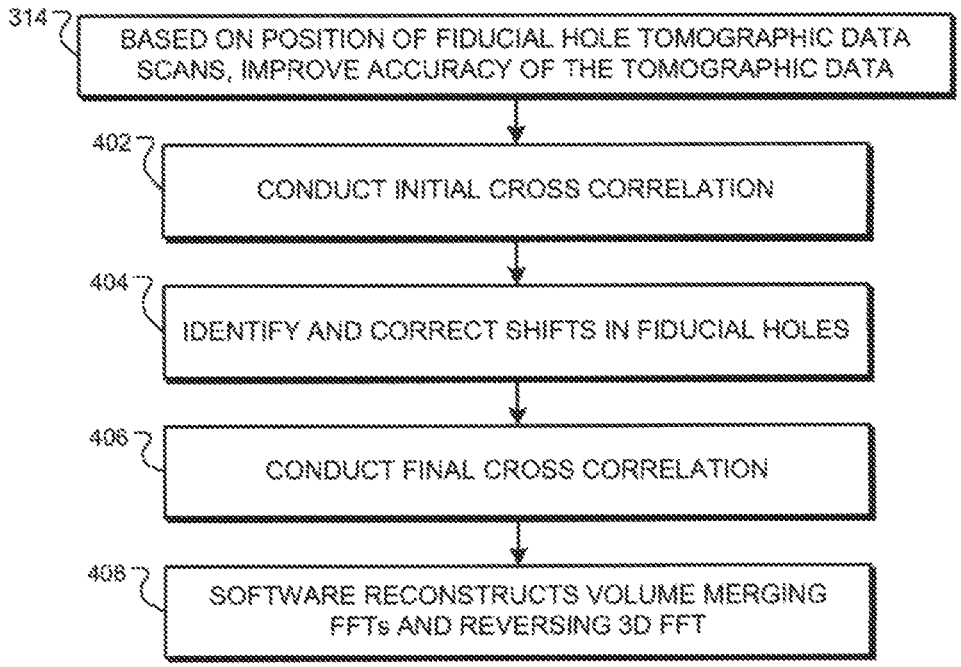
FIG. 4A is a flow chart of a more detailed process for using fiducial holes to improve the accuracy of data in the tomographic data acquisitions.

FIG. 4A is a flow chart of a more detailed process for block 314 including using fiducial holes to improve the accuracy of data in the tomographic data scan. In the depicted version, the sub-process starts at block 314 and goes to block 402 where begins the alignment of individual images from the tilt-series. Block 402 conducts an initial cross-correlation of the tomographic projections according to known techniques. Next at block 404, the process identifies and corrects any shifts of the fiducial holes, preferably by identifying the holes via pattern recognition on the projection data, or by operators manually labeling the holes or searching for holes shifts between adjacent acquisitions or between respective pairs of images that may not be adjacent. The scan data is adjusted to correct the shifts and place the fiducial holes in the correct orientation and position with respect to their surrounding scans. After this, at block 406, the process conducts a final cross-correlation of the scans to correlate features that may have been erroneously correlated with non-identical features. Such error phenomenon may especially occur, for example, in scans of samples with repetitive structures such as semiconductor samples where repetitive junctions, such as adjacent transistors, appear. After the final cross-correlation, process goes to block 408, where the software reconstructs the 3D volume using tomography reconstruction techniques, preferably by taking FFTs of the scans, combining the FFTs, and a 3D reverse FFT of the combined data. Visualization techniques may also be applied to the data at this step.

Figure 4B:
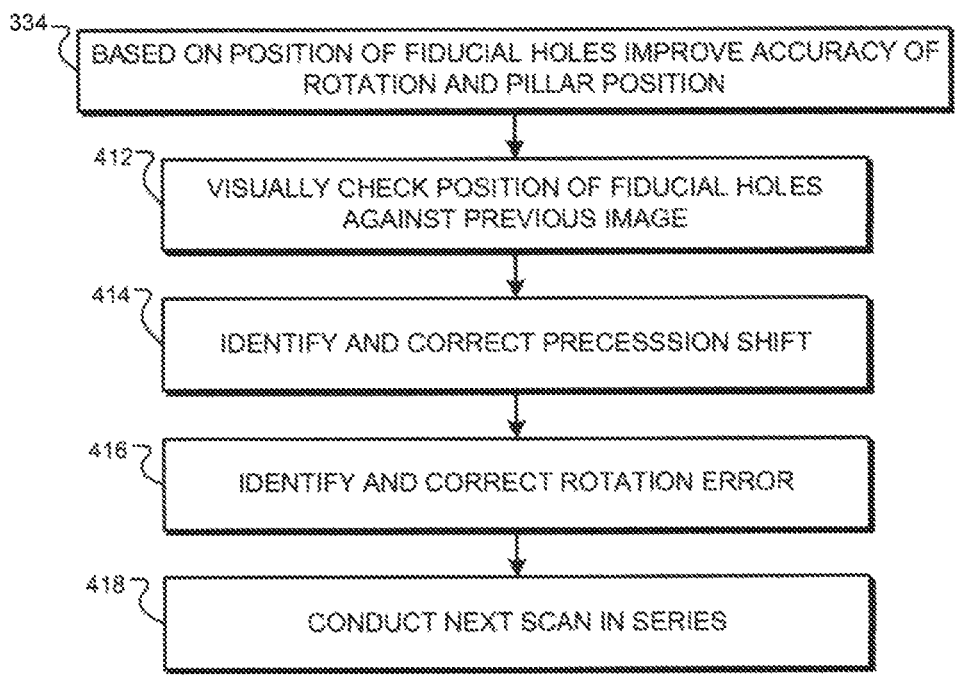
FIG. 4B is a flowchart of a more detailed process for improving sample position accuracy between successive tomographic data acquisitions.

FIG. 4B is a flowchart of a more detailed exposition of process block 334 for improving sample position accuracy between successive tomographic data scans. Such techniques may, of course, be employed to accurately position the block before the first scan in a series, and may further be employed with a "pre" scan in the desired angular position of the series first scan, with the fiducial holes employed to achieve a desired alignment for the first scan position, and the first scan then repeated. Physical correction of precession movement is typically only employed for systems in which the sample holder has mechanisms for adjustment in more dimensions than merely the rotational dimension. Precession movement typically results when pillar sample is not welded straight along the longitudinal axis of the tomography holder. A rotational sample holder having a controller configured to control suitable movement mechanisms to adjust tilt the longitudinal axis slightly between each scan, and adjust the position of the axis base in two directions perpendicular to the axis may be used to make such adjustments between each scan to compensate for a sample welded crookedly to the holder. The position adjustment process is preferably automated under control of the system controller, but may be done by cooperation with an operator. The sub-process starts at block 412 where it visually checks the position of the holes against a previous image of the sample pillar 110. The process may use the visual observation system of the TEM, or may also provide visual output of the tomography scan data so that the acquired tomography scan is used to adjust the position of the sample pillar following the rotation based on the observed position of at least one of the 1st and 2nd fiducial holes. This block may involve visual observation or automatic image processing. It may include an operator visually observing or labeling the position of one or more fiducial hole openings in a visual observation image or port, or may include visually or automatically observing or labeling the position of one or more fiducial holes in a previously acquired scan or a pre-scan of the sample.

Next at block 414 the process identifies and corrects any precession shift caused by the angular rotation, or precession misalignment in the case of the first scan in a series. Next at block 416, the process identifies and corrects over rotation, under rotation, or other undesired positional inaccuracies to place the region of interest in a desired location for the next scan in the tomographic scan series. The observation of the holes may be done automatically and software based on a designated starting position, and calculating based on the amount of angular rotation, the exact position that the 1st or 2nd fiducial hole opening ought to be observed after the rotation, and calculating a distance between that desired location and the actual observed location after the rotation. Similarly, an operator may conduct such steps by observing the location of one or more of the fiducial hole openings. Some versions may for example enable an operator to select a hole opening before the rotation begins, and the system may use image recognition techniques to identify the hole opening, and then calculate mathematically its desired location after the incremental rotation, and project such desired location on the operator's view screen so that the operator may visually detect the difference between the desired location of the hole opening, and the actual location at block 416. It is further noted, that while visual or image observation of the sample exterior is used in this example, other versions may use x-rays or preliminary lower resolution tomographic scans, or even a full resolution tomographic scan employed only for positioning purposes to correct positional errors after each successive rotation at block 416, or for the adjustment in block 414. It is noted that the observation and correction conducted in blocks 414 and 416 may be repeated for finer adjustments, for example a precession movement correction may be made, followed by a rotational correction, followed by another precession correction to correct any further error created by the rotation adjustment. Finally, at block 418 the process continues to the next scan.

Figure 4C:
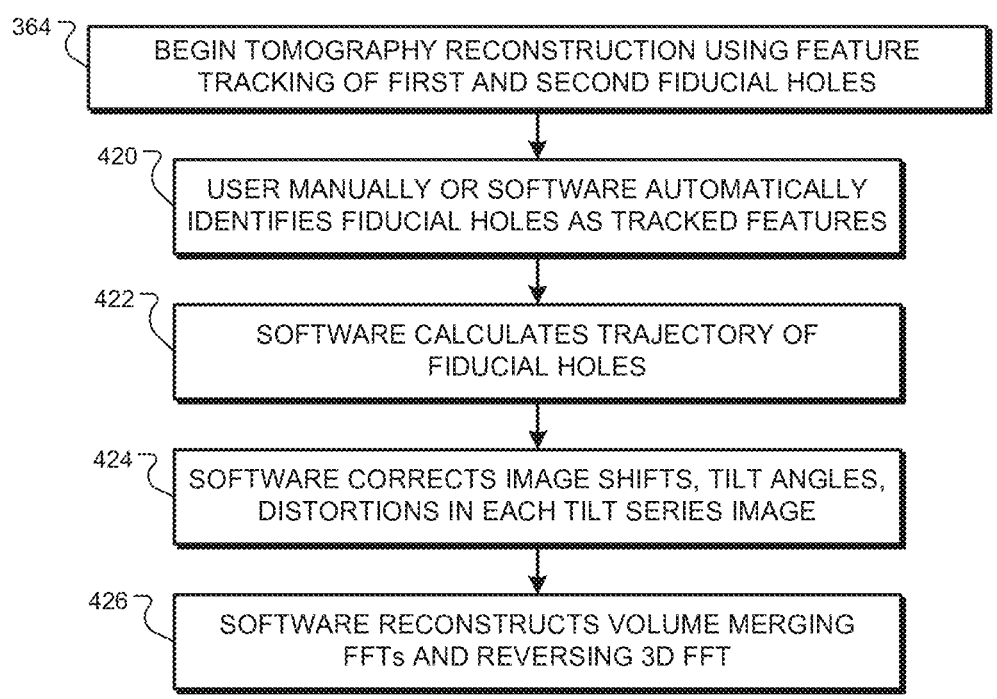
FIG. 4C is a flow chart of a more detailed process for performing tomography reconstruction using feature tracking of fiducial holes.

FIG. 4C is a flow chart of a more detailed process steps for process block 364 of performing tomography reconstruction using feature tracking of fiducial holes. Feature tracking techniques are provided in tomography systems such as those provided by the assignee of the present invention, FEI Corporation. The sub-process 364 starts with block 420 where the operator or software manually or automatically identifies the fiducial holes as features to be tracked. Such step may include identifying or providing to the feature tracking software the actual angle of the holes, such as perpendicular to the longitudinal axis. The identification may be done on one or more individual scan projections, or on a preliminary reconstruction of the data. Next, the process goes to block 422 where the software calculates or models the trajectory of the identified fiducial holes to identify their ideal position in the projected scan data. Next at block 424, the process uses the ideal positions to identify and correct image shifts, tilt angles, and distortions in each tilt scan in the series. Such features may be done in combination with the cross correlation techniques discussed herein. Finally, at block 426, the process performs the tomographic reconstruction using suitable techniques as discussed.

Figure 5:
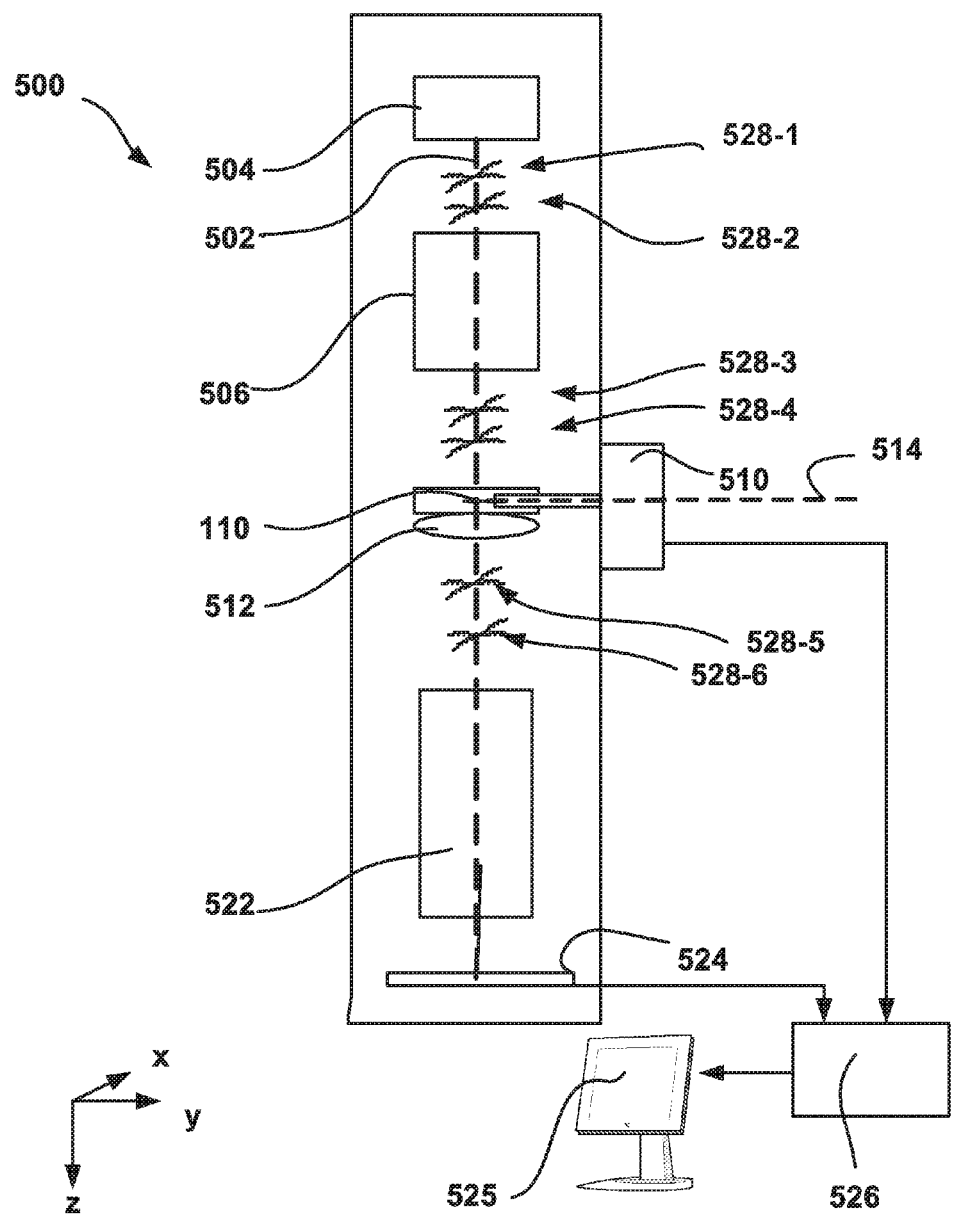
FIG. 5 is a schematic view of a TEM device employed to perform methods herein according to some embodiments.

FIG. 5 is a schematic view of a TEM device 500 employed to perform tomography according to some embodiments. As depicted, particle source 504 produces a beam of electrons along optical axis 502. The electrons have a selectable energy of typically between 80-300 keV, although higher energies, e.g. 400 keV-1 MeV, or lower energies, e.g. 50 keV, may be used. The beam of electrons is manipulated by condenser system 506 to form a parallel beam impinging on a sample 110, the sample positioned with a tilt sample holder 510. The tilt sample holder 510 ("tilt sample holder", "rotational sample holder", "tomography holder") can position the sample with respect to the optical axis and may shift the sample in the plane perpendicular to the optical axis and tilt the sample with respect to a tilt axis 514 perpendicular to the optical axis. Objective lens 512 forms a magnified image of the sample. A projection system 522 forms a magnified image of the sample on a camera system 524, thereby revealing sample details of, for example, 0.1 nm. The detector may take the form of, for example, a CCD or CMOS camera.

To align the optical components on the axis the TEM comprises a large number of deflectors, schematically shown as 528-1 through 528-6, although other deflectors on other places may be included. Tilt sample holder 510 and camera system 524 are controlled by a controller 526, the controller equipped to convert the tilt series to a 3D tomogram and to visualize the tomogram on a screen 525. It is noted that for visualization specialized software may be employed, such as the Tecnai™ Tomography Software suite provided by the assignee of the present invention, FEI Corporation.

To perform the various methods discussed herein on the electron microscope depicted in this figure, the controller 526 must be programmed to store in a memory the image acquired via camera system 524 while controlling the sample holder 510 to tilt or rotate with a controlled tilt velocity round tilt axis 514. Further, the sample stage should be able to tilt the sample over a large angle (typically −80 to +80 degrees) in order to get sufficient data to reconstruct a 3D image of the sample. The controller is able to control the position of the sample with respect to the optical axis in order to keep the volume-of-interest on the optical axis. This is done by either controlling deflectors, for example deflectors 528-3 through 528-5, or by mechanically moving the sample with respect to the stationary optical axis by controlling the sample holder 510 accordingly.

While acquiring images for the tilt series the position of the sample must be corrected so that the volume of interest stays in view and in focus. This typically demands positioning within 1 μm along the optical axis (to stay in focus) and perpendicular to the optical axis a vibration level within a camera frame time of less than a pixel (projected back to the sample), typically less than 1 nm. It is noted that deviations of the position between frames is corrected for by aligning the images forming the tilt series, as long as the volume-of-interest is kept in view. Sample holders capable of such x/y/z positioning are known, typically using piezo-actuators to achieve the required stiffness, speed and accuracy. The combination with a large angle tilt motor for smoothly rotating the sample around the tilt axis, as described in e.g. U.S. Pat. No. 7,884,326, may be employed to construct a suitable sample holder. The tilt sample holder may also be an on-axis rotation tomography holder such as the Fischione Model 2050, which accepts pillar-shaped and conically-shaped specimens and also allows 360° image acquisition without the common "missing wedge" feature in tilt holders. The On-Axis Rotation Tomography Holder features a cylindrical specimen cartridge into which a sample post is inserted, able to accept FIB-prepared specimens. The sample post containing the specimen is clamped into the specimen cartridge which fits within the body of the holder. In some versions, the TEM may include a goniometer, which is tilted through a range of motion to assist in acquiring a full tomographic tilt series. While this particular TEM design is shown, this is not limiting and any suitable TEM or STEM with tomography capability may be employed as part of the methods herein. Further, some embodiments may use a dual beam system including the milling ion beam with a TEM or STEM, while other versions may use two separate devices and transfer the sample in a sample holder.

In some embodiments, dual beam system may be used incorporating image recognition software, such as software commercially available from Cognex Corporation, Natick, Mass., to automatically identify regions of interest, and then the system can manually or automatically extract samples and create fiducial holes therein in accordance with the invention. For example, the system could automatically locate similar features on semiconductor wafers including multiple devices, and take samples of those features on different (or the same) devices, creating fiducial holes in each sample according to the techniques therein.

The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or sub-combination of the features herein.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, compositions of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of tomographic analysis of a pillar-shaped sample, comprising:
   (a) directing one or more charged particle beams at a sample to shape the sample into a pillar shape for tomography;
   (b) positioning the sample in a first position and directing one of the charged particle beams in a dwell operating mode at the sample to create a first fiducial hole in the sample;
   (c) after creating the first fiducial hole, positioning the sample for a series of tomographic data scans;
   (d) conducting a series of tomographic data scans of the sample; and
   (e) based on the position of first fiducial hole in the tomographic data scans, improving the accuracy of tomographic data in the tomographic data scans.

2. The method of claim 1 further comprising positioning the sample in a second position and directing one of the charged particle beams at the sample to create a second fiducial hole in the sample, and wherein the accuracy of tomographic data is improved based on the position of the first and second fiducial holes in the tomographic data scans.

3. The method of claim 2 wherein shaping the sample for tomography includes using a focused ion beam to form a sample pillar including a region of interest in the sample and wherein the first and second fiducial holes are positioned outside the region of interest, and further comprising positioning the sample in a third position and creating a third fiducial hole with one of the charged particle beams, and positioning the sample in a fourth position and creating a fourth fiducial hole with one of the charged particle beams, the third and fourth fiducial holes positioned outside the region of interest opposite the first and second fiducial holes.

4. The method of claim 2 wherein the first and second fiducial holes are oriented in orthogonal directions.

5. The method of claim 1 in which creating the first fiducial hole is performed in situ in a transmission electron microscope which conducts the series of tomographic data acquisitions.

6. The method of claim 1 wherein the first fiducial hole is formed holding the sample in a tilt tomography holder and the series of tomographic data acquisitions are performed by a transmission electron microscope in the tilt sample holder.

7. The method of claim 1 wherein creating the first fiducial hole includes creating a first hole passing through at least half of the sample along a first direction.

8. The method of claim 7 further comprising positioning the sample in a second position and directing one of the charged particle beams at the sample to create a second fiducial hole in the sample, and wherein the first and second holes pass entirely through the sample in their respective directions.

9. The method of claim 8 wherein the first and second holes are formed along a common plane.

10. The method of claim 1 wherein shaping the sample for tomography includes using a focused ion beam to form a sample pillar including a region of interest in the sample and the series of tomographic data scans is conducted by tilting the sample about the longitudinal axis of the pillar shape and scanning with a transmission electron microscope approximately perpendicularly to the longitudinal axis of the pillar shape.

11. The method of claim 1 wherein improving the accuracy of the tomographic data includes improving tomographic reconstruction by identifying the first fiducial hole to improve the alignment of a data set relative to relying only on cross correlation alignment.

12. The method of claim 1 wherein improving the accuracy of the tomographic data includes identifying the first fiducial hole while positioning the sample in successive ones of the series of tomographic data acquisitions.

13. The method of claim 1 wherein improving the accuracy of the tomographic data includes identifying the first fiducial hole as target features for a feature tracking technique during alignment of the tomographic dataset.

14. A method of analyzing a sample, comprising:
  (a) providing a sample in a conical or pillar shape for examination by tomography;
  (b) positioning the sample in a charged particle beam system in a first position and directing a charged particle beam at the sample to create a first fiducial;
  (c) after creating the first fiducial, positioning the sample in a microscope for a series of tomographic data scans;
  (d) conducting a series of tomographic data scans of the sample with the microscope; and
  (e) based on the position of first fiducial in the tomographic data scans, aligning data in the tomographic data acquisitions.

15. The method of claim 14 in which directing a charged particle beam at the sample to create a first fiducial comprises directing an electron beam toward the sample.

16. The method of claim 15 in which conducting a series of tomographic data scans of the sample with the microscope comprises conducting a series of tomographic data acquisitions of the sample with an electron microscope.

17. The method of claim 14 further comprising positioning the sample in the charged particle beam system in a second position and directing the charged particle beam at the sample to create a second fiducial, and in which improving the accuracy of the tomographic data is further based on the position of the second fiducial.

18. The method of claim 17 wherein the sample is a pillar having a thickness of less than 200 nm and including a region of interest, and in which the first and second fiducial are holes provided toward a first end of the region of interest, and further including forming third and fourth fiducial holes through the sample toward a second end of the region of interest opposite the first end, and in which improving the accuracy of the tomographic data is further based on the position of the third and fourth fiducial holes.

19. The method of claim 14 in which directing a charged particle beam at the sample to create a first fiducial comprises directing a charged particle beam to form a first hole in the sample.

20. The method of claim 14 in which the sample is formed in a cylindrical pillar shape and the series of tomographic data scans is conducted by tilting the sample about the longitudinal axis of the pillar shape and scanning, with the microscope, approximately perpendicularly to the longitudinal axis of the pillar shape.

21. The method of claim 14 wherein aligning data from the tomographic data includes improving tomographic reconstruction by identifying the first fiducial as a feature to be tracked with a feature tracking algorithm during an alignment procedure of the reconstruction process.

22. The method of claim 14 further comprising identifying the first fiducial while positioning the sample in successive fiducial holes of the series of tomographic data acquisitions to better position the sample.

23. A method of forming a tomographic:
  providing a pillar-shaped sample;
  after forming the pillar-shaped sample, forming a fiducial on the pillar-shaped sample;
  conducting a series of tomographic data scans of the sample with a microscope; and
  based on the position of fiducial in the tomographic data scans, aligning data in the tomographic data scans.

24. The method of claim 23 in which forming a fiducial on the pillar-shaped sample comprises forming a hold in the pillar using a charged particle beam.

25. The method of claim 23 in which aligning data in the tomographic data scans comprises aligning scans within a level.

26. The method of claim 23 in which aligning data in the tomographic data scans comprises aligning images from different levels.

* * * * *